US009437180B2

(12) United States Patent
Murgia et al.

(10) Patent No.: US 9,437,180 B2
(45) Date of Patent: Sep. 6, 2016

(54) ADAPTIVE NOISE REDUCTION USING LEVEL CUES

(71) Applicant: Knowles Electronics, LLC, Itasca, IL (US)

(72) Inventors: Carlo Murgia, Sunnyvale, CA (US); Carlos Avendano, Campbell, CA (US); Karim Younes, Menlo Park, CA (US); Mark Every, Surrey (CA); Ye Jiang, San Diego, CA (US)

(73) Assignee: Knowles Electronics, LLC, Itasca, IL (US)

( * ) Notice: Subject to any disclaimer, the term of this patent is extended or adjusted under 35 U.S.C. 154(b) by 0 days.

(21) Appl. No.: 14/222,255

(22) Filed: Mar. 21, 2014

(65) Prior Publication Data

US 2014/0205107 A1 Jul. 24, 2014

Related U.S. Application Data

(63) Continuation of application No. 12/693,998, filed on Jan. 26, 2010, now Pat. No. 8,718,290.

(51) Int. Cl.

*A61F 11/06* (2006.01)
*G10K 11/16* (2006.01)
*H04R 3/00* (2006.01)

(52) U.S. Cl.

CPC ............... *G10K 11/16* (2013.01); *H04R 3/005* (2013.01)

(58) Field of Classification Search

CPC .... H04R 3/005; H04R 3/002; H04R 25/407; H04R 2499/11; H04R 2225/43; H04R 2410/05; H04R 2430/20; H04R 25/552; H04R 25/353; H04R 1/1083; H04R 1/245; H04R 2410/01; H04R 2410/07; H04R 2499/13; G10K 11/16; G10K 11/002; H04S 2420/01

USPC .......... 381/92, 71.1–71.7, 63, 56, 94.1–94.4, 381/111, 312, 313, 71.11–71.14; 700/94; 704/226

See application file for complete search history.

(56) References Cited

U.S. PATENT DOCUMENTS 3,946,157 A 3/1976 Dreyfus
4,131,764 A 12/1978 Claasen et al.

(Continued)

FOREIGN PATENT DOCUMENTS

EP 0343792 A2 11/1989
FI 20125814 10/2012

(Continued)

OTHER PUBLICATIONS

International Search Report and Written Opinion dated May 20, 2010 in Patent Cooperation Treaty Application No. PCT/US2009/006754.

(Continued)

*Primary Examiner* — Lun-See Lao

(74) *Attorney, Agent, or Firm* — Carr & Ferrell LLP

(57) ABSTRACT

A system utilizing two pairs of microphones for noise suppression. Primary and secondary microphones may be positioned closely spaced to each other to provide acoustic signals used to achieve noise cancellation/suppression. An additional, tertiary microphone may be spaced with respect to either the primary microphone or the secondary microphone in a spread-microphone configuration for deriving level cues from audio signals provided by the tertiary and the primary or secondary microphone. The level cues are expressed via a level difference used to determine one or more cluster tracking control signal(s). The level difference-based cluster tracking signals are used to control adaptation of noise suppression. A noise cancelled primary acoustic signal and level difference-based cluster tracking control signals are used during post filtering to adaptively generate a mask to be applied to a speech estimate signal.

20 Claims, 7 Drawing Sheets

(56) References Cited

U.S. PATENT DOCUMENTS 4,630,304 A 12/1986 Borth et al.
4,766,562 A 8/1988 Vary
4,813,076 A 3/1989 Miller
4,815,023 A 3/1989 Arbeiter
4,827,443 A 5/1989 Meerkotter et al.
4,896,356 A 1/1990 Millar
4,991,166 A 2/1991 Julstrom
5,027,306 A 6/1991 Dattorro et al.
5,103,229 A 4/1992 Ribner
5,144,569 A 9/1992 Kunold
5,285,165 A 2/1994 Renfors et al.
5,323,459 A 6/1994 Hirano
5,408,235 A 4/1995 Doyle et al.
5,504,455 A 4/1996 Inkol
5,544,250 A 8/1996 Urbanski
5,583,784 A 12/1996 Kapust et al.
5,640,490 A 6/1997 Hansen et al.
5,671,287 A 9/1997 Gerzon
5,682,463 A 10/1997 Allen et al.
5,701,350 A 12/1997 Popovich
5,787,414 A 7/1998 Miike et al.
5,796,819 A 8/1998 Romesburg
5,809,463 A 9/1998 Gupta et al.
5,819,217 A 10/1998 Raman
5,839,101 A 11/1998 Vahatalo et al.
5,887,032 A 3/1999 Cioffi
5,933,495 A 8/1999 Oh
5,937,060 A 8/1999 Oh
5,937,070 A 8/1999 Todter et al.
5,956,674 A 9/1999 Smyth et al.
5,963,651 A 10/1999 Van Veen et al.
5,974,380 A 10/1999 Smyth et al.
6,011,501 A 1/2000 Gong et al.
6,018,708 A 1/2000 Dahan et al.
6,041,127 A 3/2000 Elko
6,067,517 A 5/2000 Bahl et al.
6,104,822 A 8/2000 Melanson et al.
6,160,265 A 12/2000 Bacchi et al.
6,198,668 B1 3/2001 Watts
6,226,616 B1 5/2001 You et al.
6,326,912 B1 12/2001 Fujimori
6,381,570 B2 4/2002 Li et al.
6,529,606 B1 3/2003 Jackson, Jr. II et al.
6,647,067 B1 11/2003 Hjelm et al.
6,757,652 B1 6/2004 Lund et al.
6,804,203 B1 10/2004 Benyassine et al.
6,859,508 B1 2/2005 Koyama et al.
6,915,257 B2 7/2005 Heikkinen et al.
6,934,387 B1 8/2005 Kim
6,947,509 B1 9/2005 Wong
6,954,745 B2 10/2005 Rajan
6,978,027 B1 12/2005 Dahl et al.
6,990,196 B2 1/2006 Zeng et al.
7,003,099 B1 2/2006 Zhang et al.
7,042,934 B2 5/2006 Zamir
7,050,388 B2 5/2006 Kim et al.
7,099,821 B2 8/2006 Visser et al.
7,190,665 B2 3/2007 Warke et al.
7,242,762 B2 7/2007 He et al.
7,289,554 B2 10/2007 Alloin
7,319,959 B1 1/2008 Watts
7,359,504 B1 4/2008 Reuss et al.
7,383,179 B2 6/2008 Alves et al.
7,528,679 B2 5/2009 Dick
7,555,075 B2 6/2009 Pessoa et al.
7,561,627 B2 7/2009 Chow et al.
7,577,084 B2 8/2009 Tang et al.
7,764,752 B2 7/2010 Langberg et al.
7,783,032 B2 8/2010 Abutalebi et al.
7,881,482 B2 2/2011 Christoph
7,912,567 B2 3/2011 Chhatwal et al.
7,949,522 B2 5/2011 Hetherington et al.
8,046,219 B2 10/2011 Zurek et al.
8,098,812 B2 1/2012 Fadili et al.
8,103,011 B2 1/2012 Mohammad et al.
8,107,656 B2 1/2012 Dreßler et al.
8,160,265 B2 4/2012 Mao et al.
8,180,062 B2 5/2012 Turku et al.
8,189,766 B1 5/2012 Klein
8,194,880 B2 6/2012 Avendano
8,359,195 B2 1/2013 Li
8,411,872 B2 4/2013 Stothers et al.
8,447,045 B1 5/2013 Laroche
8,473,287 B2 6/2013 Every et al.
8,526,628 B1 9/2013 Massie et al.
8,611,551 B1 12/2013 Massie et al.
8,611,552 B1 12/2013 Murgia et al.
8,718,290 B2 * 5/2014 Murgia .................. G10K 11/16 381/71.1
8,737,188 B1 5/2014 Murgia et al.
8,848,935 B1 9/2014 Massie et al.
8,934,641 B2 1/2015 Avendano et al.
8,949,120 B1 2/2015 Every et al.
9,049,282 B1 6/2015 Murgia et al.
2001/0016020 A1 8/2001 Gustafsson et al.
2001/0038323 A1 11/2001 Christensen
2001/0046304 A1 11/2001 Rast
2001/0053228 A1 12/2001 Jones
2002/0036578 A1 3/2002 Reefman
2002/0067836 A1 6/2002 Paranjpe
2003/0040908 A1 2/2003 Yang et al.
2003/0147538 A1 8/2003 Elko
2003/0169887 A1 9/2003 Fujita et al.
2003/0169891 A1 9/2003 Ryan et al.
2003/0219130 A1 11/2003 Baumgarte et al.
2003/0228019 A1 12/2003 Eichler et al.
2003/0228023 A1 12/2003 Burnett et al.
2004/0001450 A1 1/2004 He et al.
2004/0015348 A1 1/2004 McArthur et al.
2004/0042616 A1 3/2004 Matsuo
2004/0047464 A1 3/2004 Yu et al.
2004/0047474 A1 3/2004 Vries et al.
2004/0105550 A1 6/2004 Aylward et al.
2004/0111258 A1 6/2004 Zangi et al.
2004/0213416 A1 10/2004 Dahl et al.
2004/0220800 A1 11/2004 Kong et al.
2004/0247111 A1 12/2004 Popovic et al.
2004/0252772 A1 12/2004 Renfors et al.
2005/0152083 A1 7/2005 Dick
2005/0226426 A1 10/2005 Oomen et al.
2006/0053018 A1 3/2006 Engdegard et al.
2006/0093152 A1 5/2006 Thompson et al.
2006/0093164 A1 5/2006 Reams et al.
2006/0098809 A1 5/2006 Nongpiur et al.
2006/0106620 A1 5/2006 Thompson et al.
2006/0149532 A1 7/2006 Boillot et al.
2006/0160581 A1 7/2006 Beaugeant et al.
2006/0198542 A1 9/2006 Benjelloun Touimi et al.
2006/0239473 A1 10/2006 Kjorling et al.
2006/0259531 A1 11/2006 Christoph
2006/0270468 A1 11/2006 Hui et al.
2007/0008032 A1 1/2007 Kyu et al.
2007/0033020 A1 2/2007 (Kelleher) Francois et al.
2007/0041589 A1 2/2007 Patel et al.
2007/0055505 A1 3/2007 Doclo et al.
2007/0067166 A1 3/2007 Pan et al.
2007/0088544 A1 4/2007 Acero et al.
2007/0100612 A1 5/2007 Ekstrand et al.
2007/0121952 A1 5/2007 Engdegard et al.
2007/0154031 A1 7/2007 Avendano et al.
2007/0223755 A1 9/2007 Salvetti et al.
2007/0230710 A1 10/2007 Van Loon et al.
2007/0233479 A1 10/2007 Burnett
2007/0270988 A1 11/2007 Goldstein et al.
2007/0276656 A1 11/2007 Solbach et al.
2008/0019548 A1 1/2008 Avendano
2008/0025519 A1 1/2008 Yu et al.
2008/0043827 A1 2/2008 Renfors et al.
2008/0069374 A1 * 3/2008 Zhang .................... H04R 3/005 381/94.1
2008/0152157 A1 6/2008 Lin et al.
2008/0159573 A1 7/2008 Dressler et al.
2008/0162123 A1 7/2008 Goldin
2008/0170711 A1 7/2008 Breebaart et al.

(56) References Cited

U.S. PATENT DOCUMENTS

| | | | |
|---|---|---|---|
| 2008/0175422 A1 | 7/2008 | Kates | |
| 2008/0186218 A1 | 8/2008 | Ohkuri et al. | |
| 2008/0187148 A1 | 8/2008 | Itabashi et al. | |
| 2008/0201138 A1 | 8/2008 | Visser et al. | |
| 2008/0228478 A1 | 9/2008 | Hetherington et al. | |
| 2008/0247556 A1 | 10/2008 | Hess | |
| 2008/0306736 A1 | 12/2008 | Sanyal et al. | |
| 2009/0003614 A1 | 1/2009 | Neunaber | |
| 2009/0003640 A1* | 1/2009 | Burnett | G10L 21/0208 381/355 |
| 2009/0012783 A1 | 1/2009 | Klein | |
| 2009/0012786 A1 | 1/2009 | Zhang et al. | |
| 2009/0018828 A1 | 1/2009 | Nakadai et al. | |
| 2009/0063142 A1 | 3/2009 | Sukkar | |
| 2009/0080632 A1 | 3/2009 | Zhang et al. | |
| 2009/0089053 A1 | 4/2009 | Wang et al. | |
| 2009/0129610 A1 | 5/2009 | Kim et al. | |
| 2009/0154717 A1 | 6/2009 | Hoshuyama | |
| 2009/0164212 A1* | 6/2009 | Chan | G10L 21/0208 704/226 |
| 2009/0220107 A1 | 9/2009 | Every et al. | |
| 2009/0220197 A1 | 9/2009 | Gniadek et al. | |
| 2009/0238373 A1 | 9/2009 | Klein | |
| 2009/0245335 A1 | 10/2009 | Fang | |
| 2009/0245444 A1 | 10/2009 | Fang | |
| 2009/0248411 A1 | 10/2009 | Konchitsky et al. | |
| 2009/0262969 A1 | 10/2009 | Short et al. | |
| 2009/0271187 A1 | 10/2009 | Yen et al. | |
| 2009/0290736 A1 | 11/2009 | Alfsmann et al. | |
| 2009/0296958 A1 | 12/2009 | Sugiyama | |
| 2009/0302938 A1 | 12/2009 | Andersen et al. | |
| 2009/0316918 A1 | 12/2009 | Niemisto et al. | |
| 2009/0323982 A1 | 12/2009 | Solbach et al. | |
| 2010/0027799 A1 | 2/2010 | Romesburg et al. | |
| 2010/0067710 A1 | 3/2010 | Hendriks et al. | |
| 2010/0076769 A1 | 3/2010 | Yu | |
| 2010/0094643 A1 | 4/2010 | Avendano et al. | |
| 2010/0146026 A1 | 6/2010 | Christoph | |
| 2010/0158267 A1 | 6/2010 | Thormundsson et al. | |
| 2010/0246849 A1 | 9/2010 | Sudo et al. | |
| 2010/0267340 A1 | 10/2010 | Lee | |
| 2010/0272197 A1 | 10/2010 | Har et al. | |
| 2010/0272275 A1 | 10/2010 | Carreras et al. | |
| 2010/0272276 A1 | 10/2010 | Carreras et al. | |
| 2010/0290615 A1 | 11/2010 | Takahashi | |
| 2010/0290636 A1 | 11/2010 | Mao et al. | |
| 2010/0296668 A1 | 11/2010 | Lee et al. | |
| 2010/0309774 A1 | 12/2010 | Astrom | |
| 2011/0007907 A1 | 1/2011 | Park et al. | |
| 2011/0019833 A1 | 1/2011 | Kuech et al. | |
| 2011/0123019 A1 | 5/2011 | Gowreesunker et al. | |
| 2011/0158419 A1 | 6/2011 | Theverapperuma et al. | |
| 2011/0182436 A1 | 7/2011 | Murgia et al. | |
| 2011/0243344 A1 | 10/2011 | Bakalos et al. | |
| 2011/0257967 A1 | 10/2011 | Every et al. | |
| 2011/0299695 A1 | 12/2011 | Nicholson | |
| 2012/0140951 A1 | 6/2012 | Solbach et al. | |
| 2012/0237037 A1 | 9/2012 | Ninan et al. | |
| 2012/0250871 A1 | 10/2012 | Lu et al. | |
| 2016/0064009 A1 | 3/2016 | Every et al. | |

FOREIGN PATENT DOCUMENTS

| | | | |
|---|---|---|---|
| FI | 20126083 | A | 10/2012 |
| FI | FI123080 | | 10/2012 |
| JP | 2008065090 | A | 3/2008 |
| JP | 2008518257 | A | 5/2008 |
| JP | 2013518477 | A | 5/2013 |
| JP | 2013525843 | A | 6/2013 |
| JP | 5675848 | B2 | 1/2015 |
| JP | 5718251 | B2 | 3/2015 |
| KR | 1020070068270 | | 6/2007 |
| KR | 1020080109048 | | 12/2008 |
| KR | 1020120114327 | | 6/2013 |
| KR | 1020130061673 | | 6/2013 |
| TW | 200305854 | A | 11/2003 |
| TW | 200629240 | | 8/2006 |
| TW | 200705389 | | 2/2007 |
| TW | 201142829 | A | 12/2011 |
| TW | 201207845 | A | 2/2012 |
| TW | I465121 | B | 12/2014 |
| WO | WO0141504 | A1 | 6/2001 |
| WO | WO2008045476 | A2 | 4/2008 |
| WO | WO2009035614 | A1 | 3/2009 |
| WO | WO2010077361 | A1 | 7/2010 |
| WO | WO2011094232 | A1 | 8/2011 |
| WO | WO2011133405 | A1 | 10/2011 |

OTHER PUBLICATIONS

Fast Cochlea Transform, US Trademark Reg. No. 2,875,755 (Aug. 17, 2004).

International Search Report and Written Opinion dated Mar. 31, 2011 in Application No. PCT/US11/22462.

Gold et al., Theory and Implementation of the Discrete Hilbert Transform, Symposium on Computer Processing in Communications Polytechnic Institute of Brooklyn, Apr. 8-10, 1969.

Office Action mailed Apr. 8, 2014 in Japanese Patent Application 2011-544416, filed Dec. 30, 2009.

Notice of Allowance dated Nov. 25, 2014 in Japanese Application No. 2012-550214, filed Jul. 24, 2012.

Nayebi et al., "Low delay FIR filter banks: design and evaluation" IEEE Transactions on Signal Processing, vol. 42, No. 1, pp. 24-31, Jan. 1994.

Notice of Allowance mailed Feb. 17, 2015 in Japanese Patent Application No. 2011-544416, filed Dec. 30, 2009.

Office Action mailed Mar. 27, 2015 in Korean Patent Application No. 10-2011-7016591, filed Dec. 30, 2009.

Office Action mailed Apr. 17, 2015 in Taiwanese Patent Application No. 100102945, filed Jan. 26, 2011.

Office Action mailed May 11, 2015 in Finnish Patent Application 20125814, filed Jan. 25, 2011.

Office Action mailed Oct. 15, 2015 in Korean Patent Application 10-2011-7016591.

International Search Report and Written Opinion dated Apr. 9, 2008 in Patent Cooperation Treaty Application No. PCT/US2007/021654.

International Search Report and Written Opinion mailed Jul. 5, 2011 in Patent Cooperation Treaty Application No. PCT/US11/32578.

Office Action mailed Dec. 20, 2013 in Taiwan Patent Application 096146144, filed Dec. 4, 2007.

Bai et al., "Upmixing and Downmixing Two-channel Stereo Audio for Consumer Electronics". IEEE Transactions on consumer Electronics [Online] 2007, vol. 53, Issue 3, pp. 1011-1019.

Jo et al., "Crosstalk cancellation for spatial sound reproduction in portable devices with stereo loudspeakers". Communications in Computer and Information Science [Online] 2011, vol. 266, pp. 114-123.

Nongpuir et al., "NEXT cancellation system with improved convergence rate and tracking performance". IEEE Proceedings—Communications [Online] 2005, vol. 152, Issue 3, pp. 378-384.

Ahmed et al., "Blind Crosstalk Cancellation for DMT Systems" IEEE—Emergent Technologies Technical Committee. Sep. 2002. pp. 1-5.

Notice of Allowance dated Aug. 26, 2014 in Taiwan Application No. 096146144, filed Dec. 4, 2007.

Office Action mailed Oct. 30, 2014 in Korean Patent Application No. 10-2012-7027238, filed Apr. 14, 2011.

Jung et al., "Feature Extraction through the Post Processing of WFBA Based on MMSE-STSA for Robust Speech Recognition," Proceedings of the Acoustical Society of Korea Fall Conference, vol. 23, No. 2(s), pp. 39-42, Nov. 2004.

Office Action mailed Dec. 10, 2014 in Finland Patent Application No. 20126083, filed Apr. 14, 2011.

Lu et al., "Speech Enhancement Using Hybrid Gain Factor in Critical-Band-Wavelet-Packet Transform", Digital Signal Processing, vol. 17, Jan. 2007, pp. 172-188.

Office Action mailed Jun. 26, 2015 in South Korean Patent Application 1020127027238 filed Apr. 14, 2011.

(56) References Cited

OTHER PUBLICATIONS

Office Action mailed Jul. 2, 2015 in Finland Patent Application 20126083 filed Apr. 14, 2011.
Office Action mailed Jun. 23, 2015 in Japan Patent Application 2013-506188 filed Apr. 14, 2011.
Office Action mailed Oct. 29, 2015 in Korean Patent Application 1020127027238, filed Apr. 14, 2011.
Notice of Allowance, mailed Sep. 25, 2000, U.S. Appl. No. 09/356,485, filed Jul. 19, 1999.
Non-Final Office Action, mailed Jan. 10, 2007, U.S. Appl. No. 10/439,284, filed May 14, 2003.
Final Office Action, mailed May 24, 2007, U.S. Appl. No. 10/439,284, filed May 14, 2003.
Advisory Action, mailed Aug. 6, 2007, U.S. Appl. No. 10/439,284, filed May 14, 2003.
Notice of Allowance, mailed Sep. 14, 2007, U.S. Appl. No. 10/439,284, filed May 14, 2003.
Non-Final Office Action, mailed Dec. 6, 2011, U.S. Appl. No. 12/319,107, filed Dec. 31, 2008.
Final Office Action, mailed Apr. 16, 2012, U.S. Appl. No. 12/319,107, filed Dec. 31, 2008.
Advisory Action, mailed Jun. 28, 2012, U.S. Appl. No. 12/319,107, filed Dec. 31, 2008.
Non-Final Office Action, mailed Jul. 2, 2012, U.S. Appl. No. 12/693,998, filed Jan. 26, 2010.
Non-Final Office Action, mailed Oct. 2, 2012, U.S. Appl. No. 12/906,009, filed Oct. 15, 2010.
Final Office Action, mailed Dec. 19, 2012, U.S. Appl. No. 12/693,998, filed Jan. 26, 2010.
Non-Final Office Action, mailed Feb. 1, 2013, U.S. Appl. No. 12/841,061, filed Jul. 21, 2010.
Advisory Action, mailed Feb. 19, 2013, U.S. Appl. No. 12/693,998, filed Jan. 26, 2010.
Advisory Action, mailed Mar. 7, 2013, U.S. Appl. No. 12/693,998, filed Jan. 26, 2010.
Non-Final Office Action, mailed Mar. 14, 2013, U.S. Appl. No. 12/896,378, filed Oct. 1, 2010.
Final Office Action, mailed Jun. 6, 2013, U.S. Appl. No. 12/841,061, filed Jul. 21, 2010.
Non-Final Office Action, mailed Jul. 2, 2013, U.S. Appl. No. 12/906,009, filed Oct. 15, 2010.
Final Office Action, mailed Oct. 10, 2013, U.S. Appl. No. 12/896,378, filed Oct. 1, 2010.
Notice of Allowance, mailed Dec. 31, 2013, U.S. Appl. No. 12/693,998, filed Jan. 26, 2010.
Non-Final Office Action, mailed Jan. 3, 2014, U.S. Appl. No. 12/319,107, filed Dec. 31, 2008.
Final Office Action, mailed May 7, 2014, U.S. Appl. No. 12/906,009, filed Oct. 15, 2010.
Non-Final Office Action, mailed Jun. 5, 2014, U.S. Appl. No. 12/896,378, filed Oct. 1, 2010.
Non-Final Office Action, mailed Aug. 1, 2014, U.S. Appl. No. 12/841,061, filed Jul. 21, 2010.
Notice of Allowance, mailed Aug. 25, 2014, U.S. Appl. No. 12/319,107, filed Dec. 31, 2008.
Final Office Action, mailed Feb. 19, 2015, U.S. Appl. No. 12/841,061, filed Jul. 21, 2010.
Non-Final Office Action, mailed Apr. 21, 2015, U.S. Appl. No. 12/906,009, filed Oct. 15, 2010.
Final Office Action, mailed May 26, 2015, U.S. Appl. No. 13/397,597, filed Feb. 15, 2012.
Final Office Action, mailed Jul. 1, 2015, U.S. Appl. No. 12/896,378, filed Oct. 1, 2010.
Non-Final Office Action, mailed Apr. 7, 2011, U.S. Appl. No. 11/699,732, filed Jan. 29, 2007.
Final Office Action, mailed Dec. 6, 2011, U.S. Appl. No. 11/699,732, filed Jan. 29, 2007.
Advisory Action, mailed Feb. 14, 2012, U.S. Appl. No. 11/699,732, filed Jan. 29, 2007.
Notice of Allowance, mailed Mar. 15, 2012, U.S. Appl. No. 11/699,732, filed Jan. 29, 2007.
Non-Final Office Action, mailed Dec. 30, 2011, U.S. Appl. No. 12/422,917, filed Apr. 13, 2009.
Final Office Action, mailed May 14, 2012, U.S. Appl. No. 12/422,917, filed Apr. 13, 2009.
Advisory Action, mailed Jul. 27, 2012, U.S. Appl. No. 12/422,917, filed Apr. 13, 2009.
Notice of Allowance, mailed Sep. 11, 2014, U.S. Appl. No. 12/422,917, filed Apr. 13, 2009.
Non-Final Office Action, mailed May 14, 2012, U.S. Appl. No. 12/832,901, filed Jul. 8, 2010.
Final Office Action, mailed Sep. 5, 2012, U.S. Appl. No. 12/832,901, filed Jul. 8, 2010.
Final Office Action, mailed Nov. 30, 2012, U.S. Appl. No. 12/832,901, filed Jul. 8, 2010.
Notice of Allowance, mailed Mar. 4, 2013, U.S. Appl. No. 12/832,901, filed Jul. 8, 2010.
Non-Final Office Action, mailed Nov. 25, 2015, U.S. Appl. No. 12/841,061, filed Jul. 21, 2010.
Notice of Allowance, mailed Mar. 14, 2016, U.S. Appl. No. 12/841,061, filed Jul. 21, 2010.
Non-Final Office Action, mailed Apr. 25, 2013, U.S. Appl. No. 12/854,095, filed Aug. 10, 2010.
Final Office Action, mailed Oct. 21, 2013, U.S. Appl. No. 12/854,095, filed Aug. 10, 2010.
Final Office Action, mailed Oct. 22, 2013, U.S. Appl. No. 12/854,095, filed Aug. 10, 2010.
Non-Final Office Action, mailed Oct. 6, 2014, U.S. Appl. No. 12/854,095, filed Aug. 10, 2010.
Final Office Action, mailed Aug. 11, 2015, U.S. Appl. No. 12/854,095, filed Aug. 10, 2010.
Non-Final Office Action, mailed Dec. 12, 2012, U.S. Appl. No. 12/868,417, filed Aug. 25, 2010.
Final Office Action, mailed Mar. 19, 2013, U.S. Appl. No. 12/868,417, filed Aug. 25, 2010.
Notice of Allowance, mailed Aug. 2, 2013, U.S. Appl. No. 12/868,417, filed Aug. 25, 2010.
Non-Final Office Action, mailed Jun. 18, 2013, U.S. Appl. No. 12/950,431, filed Nov. 19, 2010.
Non-Final Office Action, mailed Nov. 20, 2013, U.S. Appl. No. 12/950,431, filed Nov. 19, 2010.
Notice of Allowance, mailed Jun. 5, 2014, U.S. Appl. No. 12/950,431, filed Nov. 19, 2010.
Non-Final Office Action, mailed Aug. 15, 2012, U.S. Appl. No. 13/493,648, filed Jun. 11, 2012.
Final Office Action, mailed Jan. 11, 2013, U.S. Appl. No. 13/493,648, filed Jun. 11, 2012.
Advisory Action, mailed Apr. 1, 2013, U.S. Appl. No. 13/493,648, filed Jun. 11, 2012.
Notice of Allowance, mailed Apr. 22, 2013, U.S. Appl. No. 13/493,648, filed Jun. 11, 2012.
Non-Final Office Action, mailed Jan. 9, 2012, U.S. Appl. No. 13/664,299, filed Oct. 30, 2012.
Non-Final Office Action, mailed Dec. 28, 2012, U.S. Appl. No. 13/664,299, filed Oct. 30, 2012.
Non-Final Office Action, mailed Mar. 7, 2013, U.S. Appl. No. 13/664,299, filed Oct. 30, 2012.
Final Office Action, mailed Apr. 29, 2013, U.S. Appl. No. 13/664,299, filed Oct. 30, 2012.
Non-Final Office Action, mailed Nov. 27, 2013, U.S. Appl. No. 13/664,299, filed Oct. 30, 2012.
Notice of Allowance, mailed Jan. 30, 2014, U.S. Appl. No. 13/664,299, filed Oct. 30, 2012.
Notice of Allowance, mailed Oct. 9, 2013, U.S. Appl. No. 13/935,847, filed Jul. 5, 2013.
Non-Final Office Action, mailed Jul. 10, 2014, U.S. Appl. No. 14/279,092, filed May 15, 2014.
Notice of Allowance, mailed Jan. 29, 2015, U.S. Appl. No. 14/279,092, filed May 15, 2014.
Non-Final Office Action, mailed Nov. 2, 2015, U.S. Appl. No. 14/850,911, filed Sep. 10, 2015.
Non-Final Office Action, mailed Feb. 22, 2016, U.S. Appl. No. 14/850,911, filed Sep. 10, 2015.

* cited by examiner

ADAPTIVE NOISE REDUCTION USING LEVEL CUES

CROSS REFERENCE TO RELATED APPLICATION

This application is a continuation of U.S. application Ser. No. 12/693,998, filed Jan. 26, 2010. The disclosure of the aforementioned application is incorporated herein by reference.

BACKGROUND OF THE INVENTION

Methods exist for reducing background noise in an adverse audio environment. One such method is to use a stationary noise suppression system. The stationary noise suppression system will always provide an output noise that is a fixed amount lower than the input noise. Typically, the stationary noise suppression is in the range of 12-13 decibels (dB). The noise suppression is fixed to this conservative level in order to avoid producing speech distortion, which will be apparent with higher noise suppression.

Some prior art systems invoke a generalized side-lobe canceller. The generalized side-lobe canceller is used to identify desired signals and interfering signals comprised by a received signal. The desired signals propagate from a desired location and the interfering signals propagate from other locations. The interfering signals are subtracted from the received signal with the intention of cancelling interference.

Previous audio devices have incorporated two microphone systems to reduce noise in an audio signal. A two microphone system can be used to achieve noise cancellation or source localization, but is not suitable for obtaining both. With two widely spaced microphones, it is possible to derive level difference cues for source localization and multiplicative noise suppression. However, with two widely spaced microphones, noise cancellation is limited to dry point sources given the lower coherence of the microphone signals. The two microphones can be closely spaced for improved noise cancellation due to higher coherence between the microphone signals. However, decreasing the spacing results in level cues which are too weak to be reliable for localization.

SUMMARY OF THE INVENTION

The present technology involves the combination of two independent but complementary two-microphone signal processing methodologies, an inter-microphone level difference method and a null processing noise subtraction method, which help and complement each other to maximize noise reduction performance. Each two-microphone methodology or strategy may be configured to work in optimal configuration and may share one or more microphones of an audio device.

An exemplary microphone placement may use two sets of two microphones for noise suppression, wherein the set of microphones include two or more microphones. A primary microphone and secondary microphone may be positioned closely spaced to each other to provide acoustic signals used to achieve noise cancellation. A tertiary microphone may be spaced with respect to either the primary microphone or the secondary microphone (or, may be implemented as either the primary microphone or the secondary microphone rather than a third microphone) in a spread-microphone configuration for deriving level cues from audio signals provided by tertiary and primary or secondary microphone. The level cues are expressed via an inter-microphone level difference (ILD) which is used to determine one or more cluster tracking control signals. A noise cancelled primary acoustic signal and the ILD based cluster tracking control signals are used during post filtering to adaptively generate a mask to be applied against a speech estimate signal.

An embodiment for noise suppression may receive two or more signals. The two or more signals may include a primary acoustic signal. A level difference may be determined from any pair of the two or more acoustic signals. Noise cancellation may be performed on the primary acoustic signal by subtracting a noise component from the primary acoustic signal. The noise component may be derived from an acoustic signal other than the primary acoustic signal An embodiment of a system for noise suppression may include a frequency analysis module, an ILD module, and at least one noise subtraction module, all of which may be stored in memory and executed by a processor. The frequency analysis module may be executed to receive two or more acoustic signals, wherein the two or more acoustic signals include a primary acoustic signal. The ILD module may be executed to determine a level difference cue from any pair of the two or more acoustic signals. The noise subtraction module may be executed to perform noise cancellation on the primary acoustic signal by subtracting a noise component from the primary acoustic signal. The noise component may be derived from an acoustic signal other than the primary acoustic signal.

An embodiment may include a non-transitory machine readable medium having embodied thereon a program. The program may provide instructions for a method for suppressing noise as described above.

DESCRIPTION OF EXEMPLARY EMBODIMENTS

Two independent but complementary two-microphone signal processing methodologies, an inter-microphone level difference method and a null processing noise subtraction method, can be combined to maximize noise reduction performance. Each two-microphone methodology or strategy may be configured to work in optimal configuration and may share one or more microphones of an audio device.

An audio device may utilize two pairs of microphones for noise suppression. A primary and secondary microphone may be positioned closely spaced to each other and may provide audio signals utilized for achieving noise cancellation. A tertiary microphone may be spaced in spread-microphone configuration with either the primary or secondary microphone and may provide audio signals for deriving level cues. The level cues are encoded in the inter-microphone level difference (ILD) and normalized by a cluster tracker to account for distortions due to the acoustic structures and transducers involved. Cluster tracking and level difference determination are discussed in more detail below.

In some embodiments, the ILD cue from a spread-microphone pair may be normalized and used to control the adaptation of noise cancellation implemented with the primary microphone and secondary microphone. In some embodiments, a post-processing multiplicative mask may be implemented with a post-filter. The post-filter can be derived in several ways, one of which may involve the derivation of a noise reference by null-processing a signal received from the tertiary microphone to remove a speech component.

Embodiments of the present technology may be practiced on any audio device that is configured to receive sound such as, but not limited to, cellular phones, phone handsets, headsets, and conferencing systems. Advantageously, exemplary embodiments are configured to provide improved noise suppression while minimizing speech distortion. While some embodiments of the present technology will be described in reference to operation on a cellular phone, the present technology may be practiced on any audio device.

Figure 1:
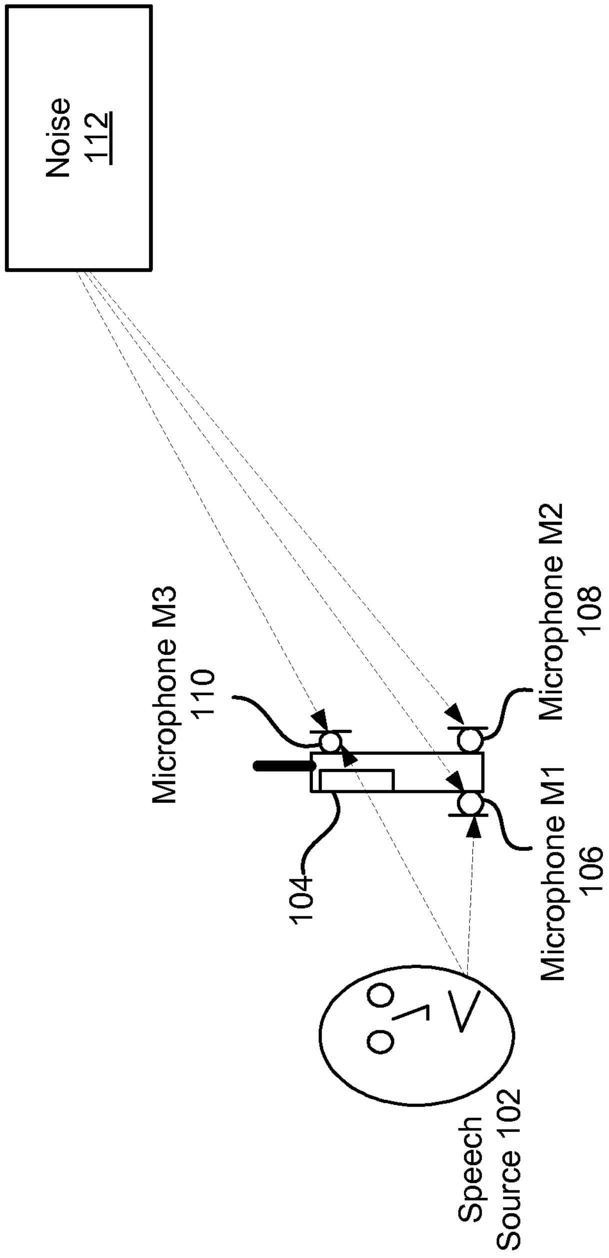
FIGS. 1 and 2 are illustrations of environments in which embodiments of the present technology may be used.
Figure 2:
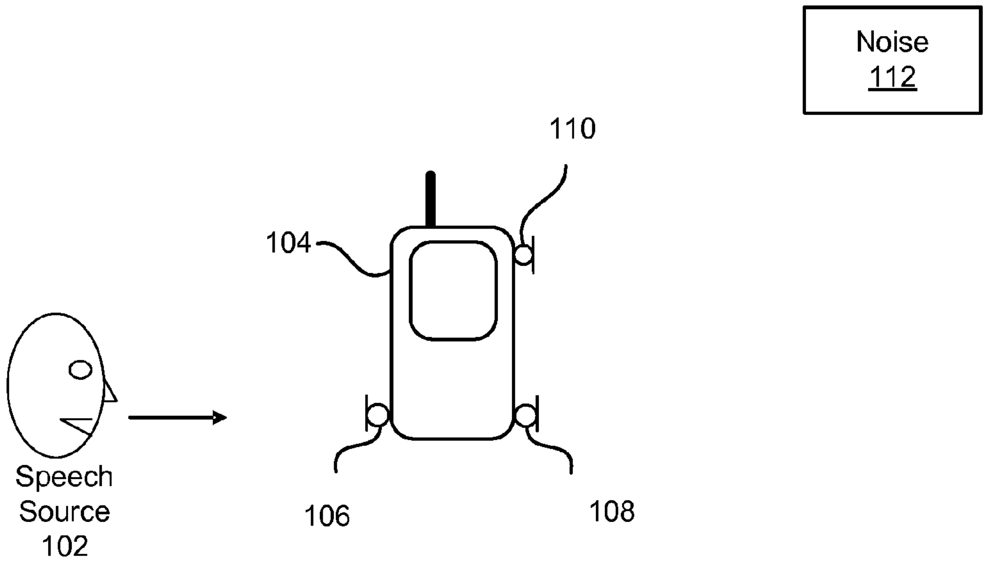

Referring to FIGS. 1 and 2, environments in which embodiments of the present technology may be practiced are shown. A user may act as a speech source 102 to an audio device 104. The exemplary audio device 104 may include a microphone array having microphones 106, 108, and 110. The microphone array may include a close microphone array with microphones 106 and 108 and a spread microphone array with microphones 110 and either microphone 106 or 108. One or more of microphones 106, 108, and 110 may be implemented as omni-directional microphones. Microphones M1, M2, and M3 can be placed at any distance with respect to each other, such as for example between 2 and 20 cm from each other.

Microphones 106, 108, and 110 may receive sound (i.e., acoustic signals) from the speech source 102 and noise 112. Although the noise 112 is shown coming from a single location in FIG. 1, the noise 112 may comprise any sounds from one or more locations different than the speech source 102, and may include reverberations and echoes. The noise 112 may be stationary, non-stationary, or a combination of both stationary and non-stationary noise.

The positions of microphones 106, 108, and 110 on audio device 104 may vary. For example in FIG. 1, microphone 110 is located on the upper backside of audio device 104 and microphones 106 and 108 are located in line on the lower front and lower back of audio device 104. In the embodiment of FIG. 2, microphone 110 is positioned on an upper side of audio device 104 and microphones 106 and 108 are located on lower sides of the audio device.

Microphones 106, 108, and 110 are labeled as M1, M2, and M3, respectively. Though microphones M1 and M2 may be illustrated as spaced closer to each other and microphone M3 may be spaced further apart from microphones M1 and M2, any microphone signal combination can be processed to achieve noise cancellation and determine level cues between two audio signals. The designations of M1, M2, and M3 are arbitrary with microphones 106, 108 and 110 in that any of microphones 106, 108 and 110 may be M1, M2, and M3. Processing of the microphone signals is discussed in more detail below with respect to FIGS. 4A-5.

The three microphones illustrated in FIGS. 1 and 2 represent an exemplary embodiment. The present technology may be implemented using any number of microphones, such as for example two, three, four, five, six, seven, eight, nine, ten or even more microphones. In embodiments with two or more microphones, signals can be processed as discussed in more detail below, wherein the signals can be associated with pairs of microphones, wherein each pair may have different microphones or may share one or more microphones.

Figure 3:
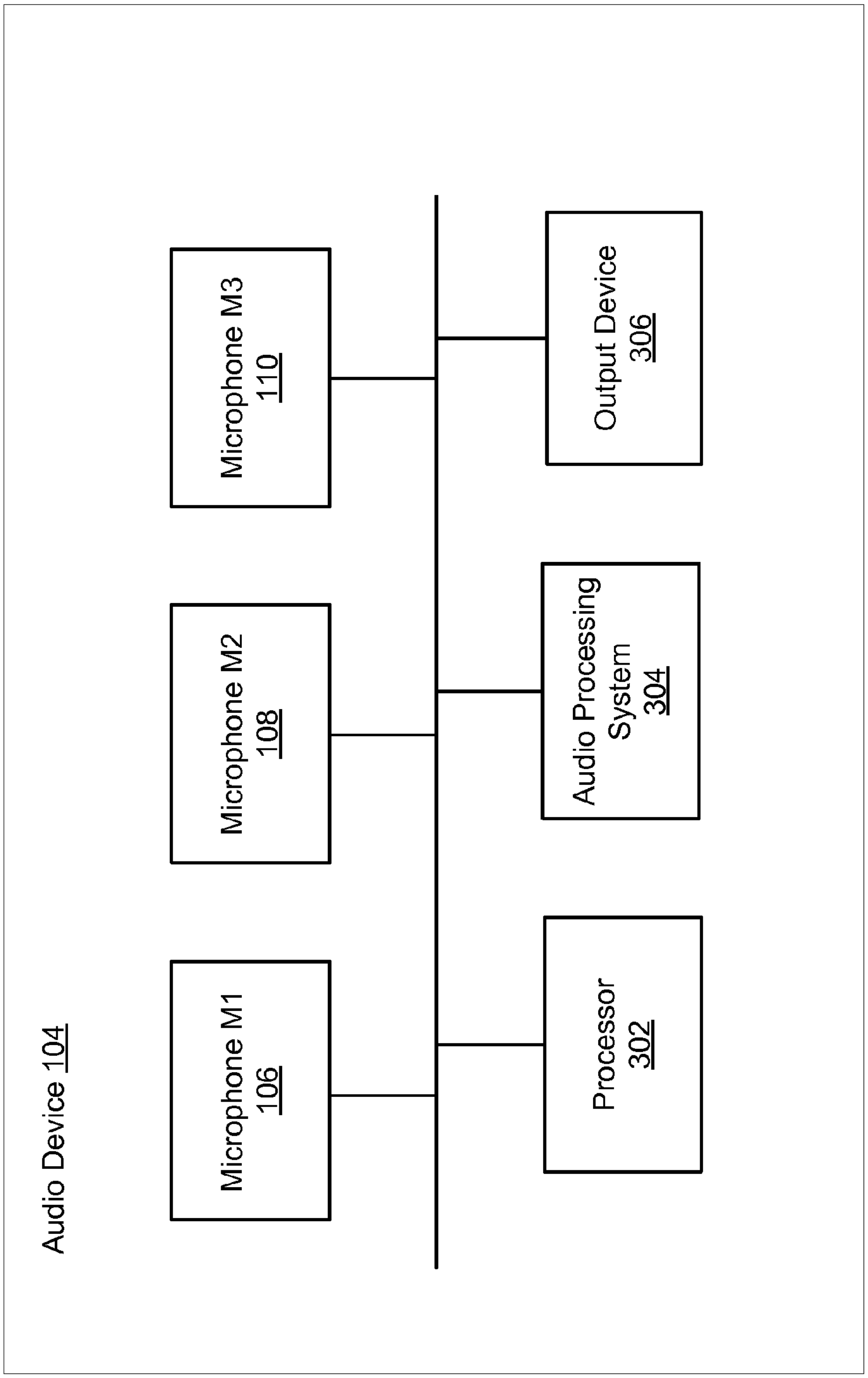
FIG. 3 is a block diagram of an exemplary audio device.

FIG. 3 is a block diagram of an exemplary audio device. In exemplary embodiments, the audio device 104 is an audio receiving device that includes microphone 106, microphone 108, microphone 110, processor 302, audio processing system 304, and output device 306. The audio device 104 may include further components (not shown) necessary for audio device 104 operations, for example components such as an antenna, interfacing components, non-audio input, memory, and other components.

Processor 302 may execute instructions and modules stored in a memory (not illustrated in FIG. 3) of audio device 104 to perform functionality described herein, including noise suppression for an audio signal.

Audio processing system 304 may process acoustic signals received by microphones 106, 108 and 110 (M1, M2 and M3) to suppress noise in the received signals and provide an audio signal to output device 306. Audio processing system 304 is discussed in more detail below with respect to FIG. 3.

The output device 306 is any device which provides an audio output to the user. For example, the output device 306 may comprise an earpiece of a headset or handset, or a speaker on a conferencing device.

Figure 4A:
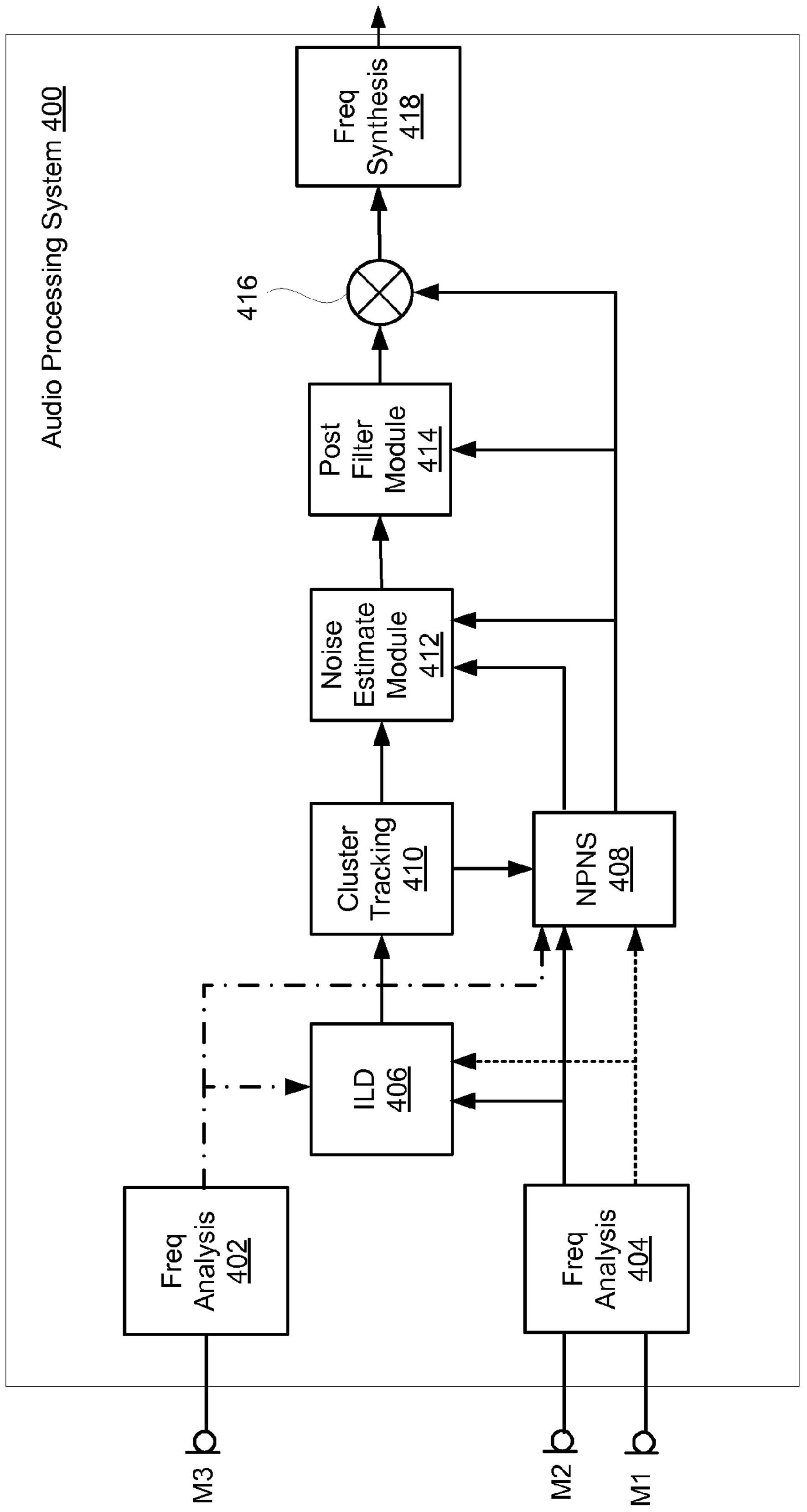
FIG. 4A is a block diagram of an exemplary audio processing system.

FIG. 4A is a block diagram of an exemplary audio processing system 400, which is an embodiment of audio processing system 304 in FIG. 3. In exemplary embodiments, the audio processing system 400 is embodied within a memory device within audio device 104. Audio processing system 400 may include frequency analysis modules 402 and 404, ILD module 406, null processing noise subtraction (NPNS) module 408, cluster tracking 410, noise estimate module 412, post filter module 414, multiplier (module) 416 and frequency synthesis module 418. Audio processing system 400 may include more or fewer components than illustrated in FIG. 4A, and the functionality of modules may be combined or expanded into fewer or additional modules. Exemplary lines of communication are illustrated between various modules of FIG. 4A and other figures, such as FIGS. 4B and 5. The lines of communication are not intended to limit which modules are communicatively coupled with others. Moreover, the visual indication of a line (e.g., dashed, dotted, alternate dash and dot) is not intended to indicate a particular communication, but rather to aid in visual presentation of the system.

In operation, acoustic signals are received by microphones M1, M2 and M3, converted to electric signals, and the electric signals are processed through frequency analysis modules 402 and 404. In one embodiment, the frequency analysis module 402 takes the acoustic signals and mimics the frequency analysis of the cochlea (i.e., cochlear domain) simulated by a filter bank. Frequency analysis module 402 may separate the acoustic signals into frequency sub-bands. A sub-band is the result of a filtering operation on an input signal where the bandwidth of the filter is narrower than the bandwidth of the signal received by the frequency analysis module 402. Alternatively, other filters such as short-time Fourier transform (STFT), sub-band filter banks, modulated complex lapped transforms, cochlear models, wavelets, etc., can be used for the frequency analysis and synthesis. Because most sounds (e.g., acoustic signals) are complex and comprise more than one frequency, a sub-band analysis on the acoustic signal determines what individual frequencies are present in the complex acoustic signal during a frame (e.g., a predetermined period of time). For example, the length of a frame may be 4 ms, 8 ms, or some other length of time. In some embodiments there may be no frame at all. The results may comprise sub-band signals in a fast cochlea transform (FCT) domain.

The sub-band frame signals are provided from frequency analysis modules 402 and 404 to ILD (module) 406 and NPNS module 408. NPNS module 408 may adaptively subtract out a noise component from a primary acoustic signal for each sub-band. As such, output of the NPNS 408 includes sub-band estimates of the noise in the primary signal and sub-band estimates of the speech (in the form of a noise-subtracted sub-band signals) or other desired audio in the primary signal.

Figure 4B:
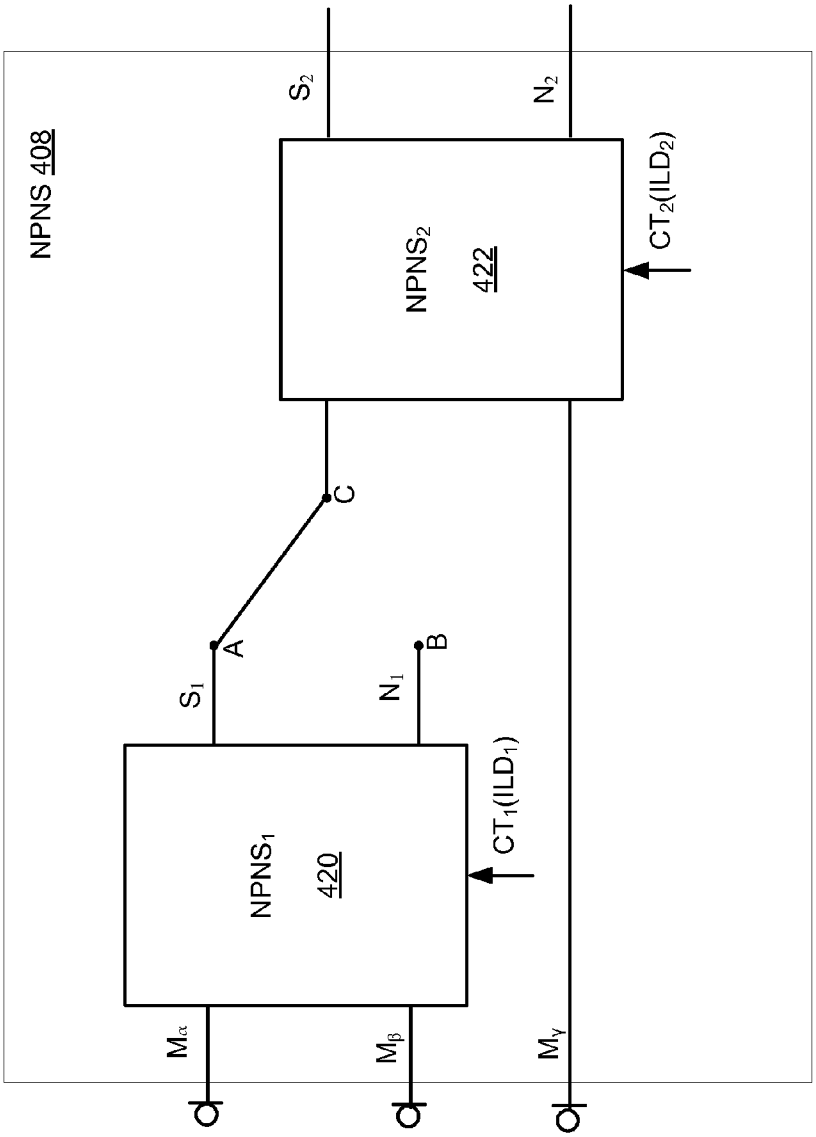
FIG. 4B is a block diagram of an exemplary null processing noise subtraction module.

FIG. 4B illustrates an exemplary implementation of NPNS module 408. NPNS module 408 may be implemented as a cascade of blocks 420 and 422, also referred to herein as NPNS 420 and NPNS 422, and as $NPNS_1$ 420 and $NPNS_2$ 422, respectively. Sub-band signals associated with two microphones are received as inputs to the first block NPNS 420. Sub-band signals associated with a third microphone are received as input to the second block NPNS 422, along with an output of the first block. The sub-band signals are represented in FIG. 4B as $M_\alpha$, $M_\beta$, and $M_\gamma$, such that:

$$\alpha, \beta, \gamma \in [1, 2, 3], \alpha \neq \beta \neq \gamma.$$

Each of $M_\alpha$, $M_\beta$, and $M_\gamma$ can be associated with any of microphones 106, 108 and 110 of FIGS. 1 and 2. NPNS 420 receives the sub-band signals with any two microphones, represented as $M_\alpha$ and $M_\beta$. NPNS 420 may also receive a cluster tracker realization signal $CT_1$ from cluster tracking module 410. NPNS 420 performs noise cancellation and generates outputs of a speech reference output $S_1$ and noise reference output $N_1$ at points A and B, respectively.

NPNS 422 may receive inputs of sub-band signals of $M_\gamma$ and the output of NPNS 420. When NPNS 422 receives the noise reference output from NPNS 420 (point C is coupled to point A), NPNS 422 performs null processing noise subtraction and generates outputs of a second speech reference output $S_2$ and second noise reference output $N_2$. These outputs are provided as output by NPNS 408 in FIG. 4A such that $S_2$ is provided to post filter module 414 and multiplier (module) 416 while $N_2$ is provided to noise estimate module 412 (or directly to post filter module 414).

Different variations of one or more NPNS modules may be used to implement NPNS 408. In some embodiments, NPNS 408 may be implemented with a single NPNS module 420. In some embodiments, a second implementation of NPNS 408 can be provided within audio processing system 400 wherein point C is connected to point B, such as for example the embodiment illustrated in FIG. 5 and discussed in more detail below.

An example of null processing noise subtraction as performed by an NPNS module is disclosed in U.S. patent application Ser. No. 12/215,980, entitled “System and Method for Providing Noise Suppression Utilizing Null Processing Noise Subtraction”, filed on Jun. 30, 2008, the disclosure of which is incorporated herein by reference.

Though a cascade of two noise subtraction modules is illustrated in FIG. 4B, additional noise subtraction modules may be utilized to implement NPNS 408, for example in a cascaded fashion as illustrated in FIG. 4B. The cascade of noise subtraction modules may include three, four, five, or some other number of noise subtraction modules. In some embodiments, the number of cascaded noise subtraction modules may be one less than the number of microphones (e.g., for eight microphones, there may be seven cascaded noise subtraction modules).

Returning to FIG. 4A, sub-band signals from frequency analysis modules 402 and 404 may be processed to determine energy level estimates during an interval of time. The energy estimate may be based on bandwidth of the cochlea channel and the acoustic signal. The energy level estimates may be determined by frequency analysis module 402 or 404, an energy estimation module (not illustrated), or another module such as ILD module 406.

From the calculated energy levels, an inter-microphone level difference (ILD) may be determined by an ILD module 406. ILD module 406 may receive calculated energy information for any of microphones M1, M2 or M3. The ILD module 406 may be approximated mathematically, in one embodiment, as $$ILD(t, \omega) = \left[1 - 2\frac{E_1(t, \omega)E_2(t, \omega)}{E_1^2(t, \omega) + E_2^2(t, \omega)}\right] * \operatorname{sign}(E_1(t, \omega) - E_2(t, \omega))$$

where $E_1$ is the energy level difference of two of microphones M1, M2 and M3 and $E_2$ is the energy level difference of the microphone not used for $E_1$ and one of the two microphones used for $E_1$. Both $E_1$ and $E_2$ are obtained from energy level estimates. This equation provides a bounded result between −1 and 1. For example, ILD goes to 1 when the $E_2$ goes to 0, and ILD goes to −1 when $E_1$ goes to 0. Thus, when the speech source is close to the two microphones used for $E_1$ and there is no noise, ILD=1, but as more noise is added, the ILD will change. In an alternative embodiment, the ILD may be approximated by $$ILD(t, \omega) = \frac{E_1(t, \omega)}{E_2(t, \omega)},$$

where $E_1(t,\omega)$ is the energy of a speech dominated signal and $E_2$ is the energy of a noise dominated signal. ILD may vary in time and frequency and may be bounded between −1 and 1. $ILD_1$ may be used to determine the cluster tracker realization for signals received by NPNS 420 in FIG. 4B. $ILD_1$ may be determined as follows:

$$ILD_1 = \{ILD(M_1, M_i), \text{ where } i \in [2,3]\},$$

wherein $M_1$ represents a primary microphone that is closest to a desired source, such as for example a mouth reference point, and $M_i$ represents a microphone other than the primary microphone. $ILD_1$ can be determined from energy estimates of the framed sub-band signals of the two microphones associated with the input to $NPNS_1$ 420. In some embodiments, $ILD_1$ is determined as the higher valued ILD between the primary microphone and the other two microphones.

$ILD_2$ may be used to determine the cluster tracker realization for signals received by $NPNS_2$ 422 in FIG. 4B. $ILD_2$ may be determined from energy estimates of the framed sub-band signals of all three microphones as follows:

$$ILD_2 = \{ILD_1; ILD(M_i, S_1), i \in [\beta, \gamma]; ILD(M_i, N_1), i \in [\alpha, \gamma]; ILD(S_1, N_1)\}.$$

Determining energy level estimates and inter-microphone level differences is discussed in more detail in U.S. patent application Ser. No. 11/343,524, entitled “System and method for utilizing inter-microphone level differences for Speech Enhancement," filed on Jan. 30, 2006, the disclosure of which is incorporated herein by reference.

Cluster tracking module 410, also referred to herein as cluster tracker 410, may receive level differences between energy estimates of sub-band framed signals from ILD module 406. ILD module 406 may generate ILD signals from energy estimates of microphone signals, speech or noise reference signals. The ILD signals may be used by cluster tracker 410 to control adaptation of noise cancellation as well as to create a mask by post filter 414. Examples of ILD signals that may be generated by ILD module 406 to control adaptation of noise suppression include $ILD_1$ and $ILD_2$. According to exemplary embodiments, cluster tracker 410 differentiates (i.e., classifies) noise and distracters from speech and provides the results to NPNS module 408 and post filter module 414.

ILD distortion, in many embodiments, may be created by either fixed (e.g., from irregular or mismatched microphone response) or slowly changing (e.g., changes in handset, talker, or room geometry and position) causes. In these embodiments, the ILD distortion may be compensated for based on estimates for either build-time clarification or runtime tracking. Exemplary embodiments of the present invention enables cluster tracker 410 to dynamically calculate these estimates at runtime providing a per-frequency dynamically changing estimate for a source (e.g., speech) and a noise (e.g., background) ILD.

Cluster tracker 410 may determine a global summary of acoustic features based, at least in part, on acoustic features derived from an acoustic signal, as well as an instantaneous global classification based on a global running estimate and the global summary of acoustic features. The global running estimates may be updated and an instantaneous local classification is derived based on at least the one or more acoustic features. Spectral energy classifications may then be determined based, at least in part, on the instantaneous local classification and the one or more acoustic features.

In some embodiments, cluster tracker 410 classifies points in the energy spectrum as being speech or noise based on these local clusters and observations. As such, a local binary mask for each point in the energy spectrum is identified as either speech or noise. Cluster tracker 410 may generate a noise/speech classification signal per sub-band and provide the classification to NPNS 408 to control its canceller parameters (sigma and alpha) adaptation. In some embodiments, the classification is a control signal indicating the differentiation between noise and speech. NPNS 408 may utilize the classification signals to estimate noise in received microphone energy estimate signals, such as $M_\alpha$, $M_\beta$, and $M_\gamma$. In some embodiments, the results of cluster tracker 410 may be forwarded to the noise estimate module 412. Essentially, a current noise estimate along with locations in the energy spectrum where the noise may be located are provided for processing a noise signal within audio processing system 400.

The cluster tracker 410 uses the normalized ILD cue from microphone M3 and either microphone M1 or M2 to control the adaptation of the NPNS implemented by microphones M1 and M2 (or M1, M2 and M3). Hence, the tracked ILD is utilized to derive a sub-band decision mask in post filter module 414 (applied at mask 416) that controls the adaption of the NPNS sub-band source estimate.

An example of tracking clusters by cluster tracker 410 is disclosed in U.S. patent application Ser. No. 12/004,897, entitled "System and method for Adaptive Classification of Audio Sources," filed on Dec. 21, 2007, the disclosure of which is incorporated herein by reference.

Noise estimate module 412 may receive a noise/speech classification control signal and the NPNS output to estimate the noise N(t,ω). Cluster tracker 410 differentiates (i.e., classifies) noise and distracters from speech and provides the results for noise processing. In some embodiments, the results may be provided to noise estimate module 412 in order to derive the noise estimate. The noise estimate determined by noise estimate module 412 is provided to post filter module 414. In some embodiments, post filter 414 receives the noise estimate output of NPNS 408 (output of the blocking matrix) and an output of cluster tracker 410, in which case a noise estimate module 412 is not utilized.

Post filter module 414 receives a noise estimate from cluster tracking module 410 (or noise estimate module 412, if implemented) and the speech estimate output (e.g., $S_1$ or $S_2$) from NPNS 408. Post filter module 414 derives a filter estimate based on the noise estimate and speech estimate. In one embodiment, post filter 414 implements a filter such as a Wiener filter. Alternative embodiments may contemplate other filters. Accordingly, the Wiener filter approximation may be approximated, according to one embodiment, as $$W = \left(\frac{P_s}{P_s + P_n}\right)^\alpha$$

where $P_s$ is a power spectral density of speech and $P_n$ is a power spectral density of noise. According to one embodiment, $P_n$ is the noise estimate, N(t,ω), which may be calculated by noise estimate module 412. In an exemplary embodiment, $P_s = E_1(t,\omega) - \beta N(t,\omega)$, where $E_1(t,\omega)$ is the energy at the output of NPNS 408 and N(t,ω) is the noise estimate provided by the noise estimate module 412. Because the noise estimate changes with each frame, the filter estimate will also change with each frame.

β is an over-subtraction term which is a function of the ILD. β compensates bias of minimum statistics of the noise estimate module 412 and forms a perceptual weighting. Because time constants are different, the bias will be different between portions of pure noise and portions of noise and speech. Therefore, in some embodiments, compensation for this bias may be necessary. In exemplary embodiments, β is determined empirically (e.g., 2-3 dB at a large ILD, and is 6-9 dB at a low ILD).

In the above exemplary Wiener filter equation, α is a factor which further suppresses the estimated noise components. In some embodiments, α can be any positive value. Nonlinear expansion may be obtained by setting α to 2. According to exemplary embodiments, α is determined empirically and applied when a body of W=

$$\left(\frac{P_s}{P_s + P_n}\right)$$

falls below a prescribed value (e.g., 12 dB down from the maximum possible value of W, which is unity).

Because the Wiener filter estimation may change quickly (e.g., from one frame to the next frame) and noise and speech estimates can vary greatly between each frame, application of the Wiener filter estimate, as is, may result in artifacts (e.g., discontinuities, blips, transients, etc.). Therefore, optional filter smoothing may be performed to smooth the Wiener filter estimate applied to the acoustic signals as a function of time. In one embodiment, the filter smoothing may be mathematically approximated as, $$M(t,\omega) = \lambda_s(t,\omega)W(t,\omega) + (1-\lambda_s(t,\omega))M(t-1,\omega)$$

where $\lambda_s$ is a function of the Wiener filter estimate and the primary microphone energy, $E_1$.

A second instance of the cluster tracker could be used to track the NP-ILD, such as for example the ILD between the NP-NS output (and signal from the microphone M3 or the NPNS output generated by null processing the M3 audio signal to remove the speech). The ILD may be provided as follows:

$$ILD_3=\{ILD_1;\ ILD_2;\ ILD\ (S_2, N_2);\ ILD\ (M_i, S_2),\ i \in [\beta, \gamma];\ ILD(M_i, N_2),\ i \in [\alpha, \gamma];\ ILD(S_2, N_1);\ ILD\ (S_1, N_2);\ ILD\ (S_2, \acute{N}_2)\},$$

wherein $\acute{N}_2$ is derived as the output of NPNS module 520 in FIG. 5, discussed in more detail below. After being processed by post filter module 414, the frequency sub-bands output of NPNS module 408 are multiplied at mask 416 by the Wiener filter estimate (from post filter 414) to estimate the speech. In the above Wiener filter embodiment, the speech estimate is approximated by $S(t, \omega)=X_1(t, \omega)*M(t, \omega)$, where $X_1$ is the acoustic signal output of the NPNS module 408.

Next, the speech estimate is converted back into time domain from the cochlea domain by frequency synthesis module 418. The conversion may comprise taking the masked frequency sub-bands and adding together phase shifted signals of the cochlea channels in a frequency synthesis module 418. Alternatively, the conversion may comprise taking the masked frequency sub-bands and multiplying these with an inverse frequency of the cochlea channels in the frequency synthesis module 418. Once conversion is completed, the signal is output to user via output device 306.

Figure 5:
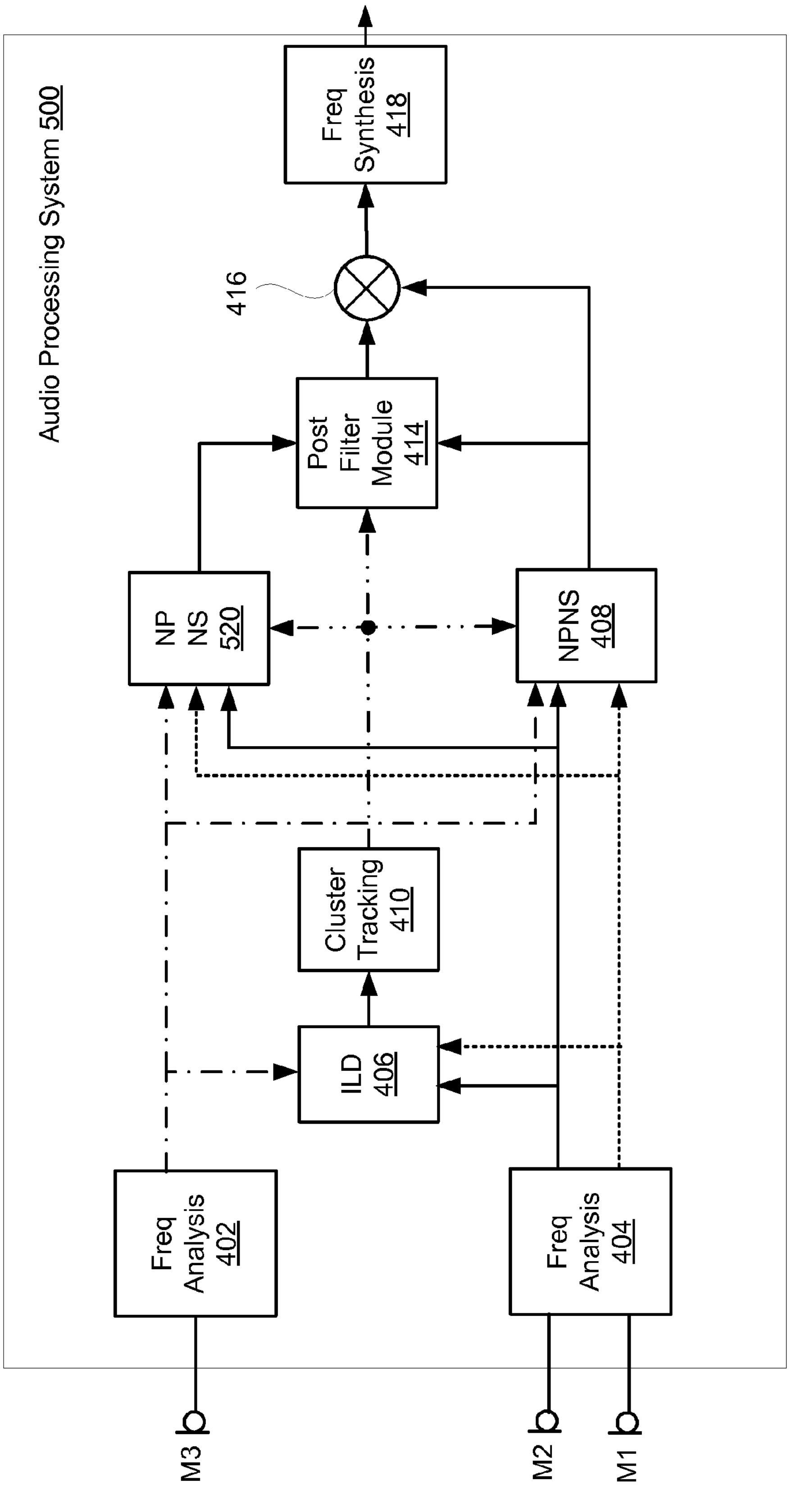
FIG. 5 is a block diagram of another exemplary audio processing system.

FIG. 5 is a block diagram of another exemplary audio processing system 500, which is another embodiment of audio processing system 304 in FIG. 3. The system of FIG. 5 includes frequency analysis modules 402 and 404, ILD module 406, cluster tracking module 410, NPNS modules 408 and 520, post filter modules 414, multiplier module 416 and frequency synthesis module 418.

The audio processing system 500 of FIG. 5 is similar to the system of FIG. 4A except that the frequency sub-bands of the microphones M1, M2 and M3 are each provided to both NPNS 408 and NPNS 520, in addition to ILD 406. ILD output signals based on received microphone frequency sub-band energy estimates are provided to cluster tracker 410, which then provides a control signal with a speech/noise indication to NPNS 408, NPNS 520 and post filter module 414.

NPNS 408 in FIG. 5 may operate in a similar manner as NPNS 408 in FIG. 4A. NPNS 520 may be implemented as NPNS 408, as illustrated in FIG. 4B, when point C is connected to point B, thereby providing a noise estimate as an input to NPNS 422. The output of NPNS 520 is a noise estimate and provided to post filter module 414.

Post filter module 414 receives a speech estimate from NPNS 408, a noise estimate from NPNS 520, and a speech/noise control signal from cluster tracker 410 to adaptively generate a mask to apply to the speech estimate at multiplier 416. The output of the multiplier is then processed by frequency synthesis module 418 and output by audio processing system 500.

Figure 6:
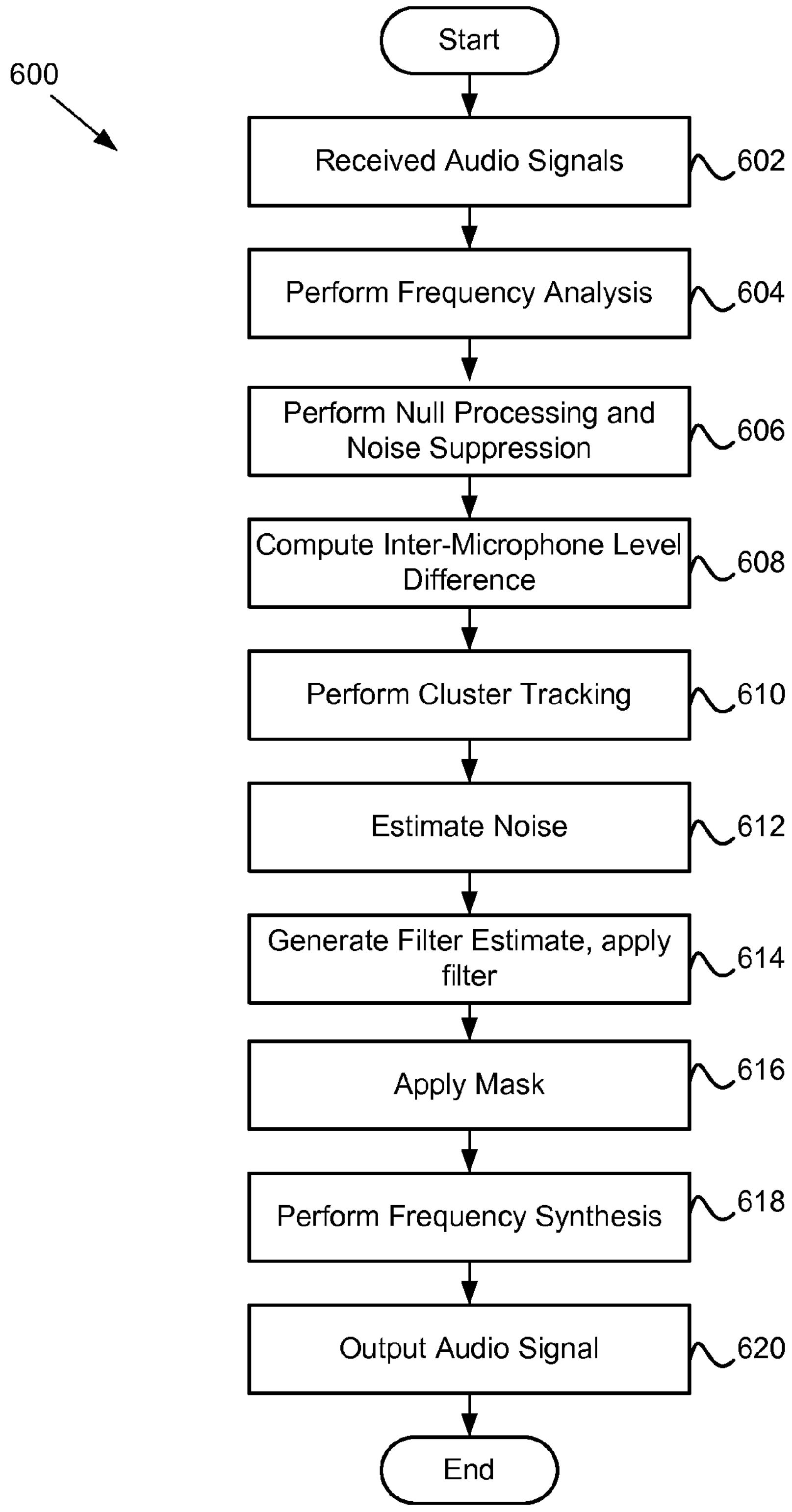
FIG. 6 is a flowchart of an exemplary method for providing an audio signal with noise reduction.

FIG. 6 is a flowchart 600 of an exemplary method for suppressing noise in an audio device. In step 602, audio signals are received by the audio device 104. In exemplary embodiments, a plurality of microphones (e.g., microphones M1, M2 and M3) receive the audio signals. The plurality of microphones may include two microphones which form a close microphone array and two microphones (one or more of which may be shared with the close microphone array microphones) which form a spread microphone array.

In step 604, the frequency analysis on the primary, secondary and tertiary acoustic signals may be performed. In one embodiment, frequency analysis modules 402 and 404 utilize a filter bank to determine frequency sub-bands for the acoustic signals received by the device microphones.

Noise subtraction and noise suppression may be performed on the sub-band signals at step 606. NPNS modules 408 and 520 may perform the noise subtraction and suppression processing on the frequency sub-band signals received from frequency analysis modules 402 and 404. NPNS modules 408 and 520 then provide frequency sub-band noise estimate and speech estimate to post filter module 414.

Inter-microphone level differences (ILD) are computed at step 608. Computing the ILD may involve generating energy estimates for the sub-band signals from both frequency analysis module 402 and frequency analysis module 404. The output of the ILD is provided to cluster tracking module 410.

Cluster tracking is performed at step 610 by cluster tracking module 410. Cluster tracking module 410 receives the ILD information and outputs information indicating whether the sub-band is noise or speech. Cluster tracking 410 may normalize the speech signal and output decision threshold information from which a determination may be made as to whether a frequency sub-band is noise or speech. This information is passed to NPNS 408 and 520 to decide when to adapt noise cancelling parameters.

Noise may be estimated at step 612. In some embodiments, the noise estimation may performed by noise estimate module 412, and the output of cluster tracking module 410 is used to provide a noise estimate to post filter module 414. In some embodiments, the NPNS module(s) 408 and/or 520 may determine and provide the noise estimate to post filter module 414.

A filter estimate is generated at step 614 by post filter module 414. In some embodiments, post filter module 414 receives an estimated source signal comprised of masked frequency sub-band signals from NPNS module 408 and an estimation of the noise signal from either NPNS 520 or cluster tracking module 410 (or noise estimate module 412). The filter may be a Wiener filter or some other filter.

A gain mask may be applied in step 616. In one embodiment, the gain mask generated by post filter 414 may be applied to the speech estimate output of NPNS 408 by the multiplier module 416 on a per sub-band signal basis.

The cochlear domain sub-bands signals may then be synthesized in step 618 to generate an output in time domain. In one embodiment, the sub-band signals may be converted back to the time domain from the frequency domain. Once converted, the audio signal may be output to the user in step 620. The output may be via a speaker, earpiece, or other similar devices.

The above-described modules may be comprised of instructions that are stored in storage media such as a non-transitory machine readable medium (e.g., a computer readable medium). The instructions may be retrieved and executed by the processor 302. Some examples of instructions include software, program code, and firmware. Some examples of storage media comprise memory devices and integrated circuits. The instructions are operational when executed by the processor 302 to direct the processor 302 to operate in accordance with embodiments of the present technology. Those skilled in the art are familiar with instructions, processors, and storage media.

The present technology is described above with reference to exemplary embodiments. It will be apparent to those skilled in the art that various modifications may be made and other embodiments may be used without departing from the broader scope of the present technology. For example, the functionality of a module discussed may be performed in separate modules, and separately discussed modules may be combined into a single module. Additional modules may be incorporated into the present technology to implement the features discussed as well variations of the features and functionality within the spirit and scope of the present technology. Therefore, these and other variations upon the exemplary embodiments are intended to be covered by the present disclosure.

What is claimed is:

1. A method for suppressing noise, the method comprising:

receiving three acoustic signals;

determining level difference information from two pairs of the acoustic signals, one of the pairs comprising a first and second acoustic signal of the three acoustic signals, another of the pairs comprising a third acoustic signal of the acoustic signals and one of the first and second acoustic signals, wherein a primary acoustic signal comprises one of the three acoustic signals; and performing noise cancellation on the primary acoustic signal by subtracting a noise component from the primary acoustic signal, the noise component based at least in part on the level difference information.

2. The method of claim 1, further comprising adapting the noise cancellation of the primary acoustic signal based at least in part on the level difference information.

3. The method of claim 1, further comprising performing noise cancellation by noise subtraction blocks configured in a cascade, the noise subtraction blocks processing any of the three acoustic signals.

4. The method of claim 3, further comprising:

receiving, by a first noise subtraction block in the cascade, the one of the pairs of the three acoustic signals; and receiving, by a next noise subtraction block in the cascade, an output of the first noise subtraction block and one of the three acoustic signals not included in the one of the pairs of the three acoustic signals received by the first noise subtraction block.

5. The method of claim 4, wherein the output of the first noise subtraction block is a noise reference signal, further comprising:

generating a noise estimate based at least in part on the noise reference signal and a speech reference output of any of the noise subtraction blocks; and providing the noise estimate to a post processor.

6. The method of claim 5, wherein the level difference information is normalized via a cluster tracker module.

7. The method of claim 1, wherein the three acoustic signals further include a secondary acoustic signal and a tertiary acoustic signal.

8. The method of claim 1, further comprising:

generating the level difference information using energy level estimates; and providing the level difference information to a cluster tracker module, the cluster tracker module being configured for controlling adaptation of noise suppression.

9. A system for suppressing noise, the system comprising:

a frequency analysis module stored in memory and executed by a processor to receive three acoustic signals;

a level difference module stored in memory and executed by a processor to determine level difference information from two pairs of acoustic signals, one of the pairs of the acoustic signals comprising a first and second acoustic signal of the three acoustic signals, another of the pairs of acoustic signals comprising a third acoustic signal of the three acoustic signals and one of the first and second acoustic signals, wherein a primary acoustic signal comprises one of the three acoustic signals; and a noise cancellation module stored in memory and executed by a processor to perform noise cancellation on the primary acoustic signal by subtracting a noise component from the primary acoustic signal, the noise component based at least in part on the level difference information.

10. The system of claim 9, wherein a post filter module is executed to adapt the noise cancellation of the primary acoustic signal based at least in part on the level difference information.

11. The system of claim 9, further comprising noise subtraction blocks configured in a cascade, the noise subtraction blocks performing noise cancellation by processing any of the three acoustic signals.

12. The system of claim 11, wherein a first noise subtraction block in the cascade, when executed by a processor, receives the one of the pairs of the three acoustic signals, and a next noise subtraction block in the cascade, when executed by a processor, receives an output of the first noise subtraction block and one of the three acoustic signals not included in the one of the pairs of the acoustic signals received by the first noise subtraction block.

13. The system of claim 12, wherein the output of the first noise subtraction block is a noise reference signal, the system further comprising a noise estimate module, which, when executed, generates a noise estimate based at least in part on the noise reference signal and a speech reference output of any noise subtraction block, and provides the noise estimate to a post processor.

14. The system of claim 13, wherein the level difference information is normalized via a cluster tracker module for controlling adaptation of noise suppression.

15. A non-transitory computer readable storage medium having embodied thereon a program, the program being executable by a processor to perform a method for suppressing noise, the method comprising:

receiving three acoustic signals;

determining level difference information from two pairs of the acoustic signals, one of the pairs comprising a first and second acoustic signal of the three acoustic signals, another of the pairs comprising a third acoustic signal of the acoustic signals and one of the first and second acoustic signals, wherein a primary acoustic signal comprises one of the three acoustic signals; and performing noise cancellation on the primary acoustic signal by subtracting a noise component from the primary acoustic signal, the noise component based at least in part on the level difference information.

16. The non-transitory computer readable storage medium of claim 15, the method further comprising adapting the noise cancellation of the primary acoustic signal based at least in part on the level difference information.

17. The non-transitory computer readable storage medium of claim 15, the method further comprising performing noise cancellation by noise subtraction blocks configured in a cascade, the noise subtraction blocks processing any of the three acoustic signals.

18. The non-transitory computer readable storage medium of claim 17, the method further comprising:

receiving, by a first noise subtraction block in the cascade, the one of the pairs of the three acoustic signals; and receiving, by a next noise subtraction block in the cascade, an output of the first noise subtraction block and one of the three acoustic signals not included in the one of the pairs of the three acoustic signals received by the first noise subtraction block.

19. The non-transitory computer readable storage medium of claim 18, wherein the output of the first noise subtraction block is a noise reference signal, the method further comprising:

generating a noise estimate based at least in part on the noise reference signal and a speech reference output of any of the noise subtraction blocks; and providing the noise estimate to a post processor, wherein the level difference information is normalized.

20. The non-transitory computer readable storage medium of claim 19, further comprising:

generating the level difference information using energy level estimates determined via at least one frequency analysis module; and providing the level difference information to a cluster tracker module, the cluster tracker module being configured to control adaptation of noise suppression.

* * * * *